United States Patent
Pacheco et al.

(10) Patent No.: US 9,750,577 B2
(45) Date of Patent: Sep. 5, 2017

(54) SINGLE HAND OPERATED REMOTE CONTROLLER FOR REMOTE CATHETER POSITIONING SYSTEM

(71) Applicant: Catheter Precision, Inc., Ledgewood, NJ (US)

(72) Inventors: Robert Pacheco, Bayside, NY (US); Steve Foley, Kerrville, TX (US); David Jenkins, Budd Lake, NJ (US); Brandon D. Guarino, Howard Beach, NY (US)

(73) Assignee: CATHETER PRECISION, INC., Ledgewood, NJ (US)

( * ) Notice: Subject to any disclaimer, the term of this patent is extended or adjusted under 35 U.S.C. 154(b) by 372 days.

(21) Appl. No.: 14/478,738

(22) Filed: Sep. 5, 2014

(65) Prior Publication Data
US 2015/0073340 A1    Mar. 12, 2015

Related U.S. Application Data

(60) Provisional application No. 61/874,434, filed on Sep. 6, 2013.

(51) Int. Cl.
*A61B 34/30* (2016.01)
*A61B 8/12* (2006.01)
(Continued)

(52) U.S. Cl.
CPC ............. *A61B 34/30* (2016.02); *A61B 8/12* (2013.01); *A61B 34/76* (2016.02); *A61B 5/6852* (2013.01);
(Continued)

(58) Field of Classification Search
CPC .......... A61B 18/1492; A61B 2017/003; A61B 2018/00297; A61B 2034/742;
(Continued)

(56) References Cited

U.S. PATENT DOCUMENTS

| 4,549,538 A | 10/1985 | Schadrack, III et al. |
| 4,721,123 A | 1/1988 | Cosentino et al. |

(Continued)

FOREIGN PATENT DOCUMENTS

| JP | 2007527296 A | 9/2007 |
| WO | 2005087128 A1 | 9/2005 |

(Continued)

OTHER PUBLICATIONS

WIPO, International Preliminary Report on Patentability; PCT/US2006/027024; Jan. 16, 2008; 8pgs.
(Continued)

*Primary Examiner* — Rebecca E Eisenberg
(74) *Attorney, Agent, or Firm* — The Marbury Law Group, PLLC

(57) ABSTRACT

Systems, methods, and devices of the various embodiments provide a remote controller for a catheter positioning system configured to be operated with a single hand by a catheter positioning system operator. In an embodiment, the remote controller may include a thumb joystick control, first wheel control, and second wheel control. In an embodiment, the remote controller may include various visual indicators and/or haptic feedback mechanisms providing information to a catheter positioning system operator.

22 Claims, 10 Drawing Sheets

(51) Int. Cl.

| | | |
|---|---|---|
| A61B 18/14 | (2006.01) | |
| A61B 17/00 | (2006.01) | |
| A61B 18/00 | (2006.01) | |
| A61B 34/00 | (2016.01) | |
| A61B 90/30 | (2016.01) | |
| A61B 90/00 | (2016.01) | |
| A61B 5/00 | (2006.01) | |

(52) U.S. Cl.
CPC ......... *A61B 5/7455* (2013.01); *A61B 18/1492* (2013.01); *A61B 90/30* (2016.02); *A61B 2017/003* (2013.01); *A61B 2017/00115* (2013.01); *A61B 2018/00839* (2013.01); *A61B 2034/301* (2016.02); *A61B 2034/742* (2016.02); *A61B 2090/0811* (2016.02)

(58) Field of Classification Search
CPC . A61B 2090/0811; A61B 34/30; A61B 34/76; A61M 2205/3569; A61M 2205/582; A61M 25/0105; A61M 25/0113
See application file for complete search history.

(56) References Cited

U.S. PATENT DOCUMENTS

| | | |
|---|---|---|
| 5,226,892 A | 7/1993 | Boswell |
| 5,644,551 A | 7/1997 | Carmichael et al. |
| 5,649,956 A | 7/1997 | Jensen et al. |
| 5,682,890 A | 11/1997 | Kormos et al. |
| 5,810,880 A | 9/1998 | Jensen et al. |
| 5,814,038 A | 9/1998 | Jensen et al. |
| 5,855,583 A | 1/1999 | Wang et al. |
| 6,007,550 A | 12/1999 | Wang et al. |
| 6,063,095 A | 5/2000 | Wang et al. |
| 6,080,181 A | 6/2000 | Jensen et al. |
| 6,096,004 A | 8/2000 | Meglan et al. |
| 6,132,368 A | 10/2000 | Cooper |
| 6,171,234 B1 | 1/2001 | White et al. |
| 6,171,277 B1 | 1/2001 | Ponzi |
| 6,200,315 B1 | 3/2001 | Gaiser et al. |
| 6,346,072 B1 | 2/2002 | Cooper |
| 6,396,232 B2 | 5/2002 | Haanpaa et al. |
| 6,398,755 B1 | 6/2002 | Belef et al. |
| 6,413,264 B1 | 7/2002 | Jensen et al. |
| 6,445,984 B1 | 9/2002 | Kellogg |
| 6,461,372 B1 | 10/2002 | Jensen et al. |
| 6,527,782 B2 | 3/2003 | Hogg et al. |
| 6,620,174 B2 | 9/2003 | Jensen et al. |
| 6,726,675 B1 | 4/2004 | Beyar |
| 6,788,999 B2 | 9/2004 | Green |
| 6,850,817 B1 | 2/2005 | Green |
| 6,963,792 B1 | 11/2005 | Green |
| 6,974,465 B2 | 12/2005 | Belef et al. |
| 6,999,852 B2 | 2/2006 | Green |
| 7,006,895 B2 | 2/2006 | Green |
| 7,090,683 B2 | 8/2006 | Brock et al. |
| 7,118,582 B1 | 10/2006 | Wang et al. |
| 7,169,141 B2 | 1/2007 | Brock et al. |
| 7,204,844 B2 | 4/2007 | Jensen et al. |
| 7,214,230 B2 | 5/2007 | Brock et al. |
| 7,276,044 B2 | 10/2007 | Ferry et al. |
| 7,314,230 B2 | 1/2008 | Kumagai et al. |
| 7,331,967 B2 | 2/2008 | Lee et al. |
| 7,357,774 B2 | 4/2008 | Cooper |
| 7,371,210 B2 | 5/2008 | Brock et al. |
| 7,377,906 B2 | 5/2008 | Selkee |
| 7,537,570 B2 | 5/2009 | Kastelein |
| 7,630,752 B2 | 12/2009 | Viswanathan |
| 7,648,513 B2 | 1/2010 | Green et al. |
| 7,758,564 B2 | 7/2010 | Long et al. |
| 8,046,049 B2 | 10/2011 | Govari et al. |
| 8,672,880 B2 | 3/2014 | Cohen et al. |
| 2001/0053879 A1 | 12/2001 | Mills et al. |
| 2002/0042620 A1 | 4/2002 | Julian et al. |
| 2002/0072704 A1 | 6/2002 | Mansouri-Ruiz |
| 2002/0120254 A1 | 8/2002 | Julian et al. |
| 2002/0177789 A1 | 11/2002 | Ferry et al. |
| 2002/0183723 A1 | 12/2002 | Belef et al. |
| 2003/0176778 A1* | 9/2003 | Messing ............... A61B 18/00 600/374 |
| 2004/0077942 A1 | 4/2004 | Hall et al. |
| 2004/0254566 A1 | 12/2004 | Plicchi et al. |
| 2005/0038412 A1 | 2/2005 | Rabiner et al. |
| 2005/0065435 A1 | 3/2005 | Rauch et al. |
| 2005/0113719 A1 | 5/2005 | Saadat |
| 2005/0203382 A1 | 9/2005 | Govari et al. |
| 2005/0209614 A1 | 9/2005 | Fenter et al. |
| 2005/0222554 A1 | 10/2005 | Wallace et al. |
| 2005/0228440 A1 | 10/2005 | Brock et al. |
| 2005/0277874 A1 | 12/2005 | Selkee |
| 2005/0283140 A1 | 12/2005 | Jensen et al. |
| 2006/0009735 A1 | 1/2006 | Viswanathan et al. |
| 2006/0041181 A1 | 2/2006 | Viswanathan et al. |
| 2006/0084911 A1 | 4/2006 | Belef et al. |
| 2006/0084945 A1 | 4/2006 | Moll et al. |
| 2006/0095022 A1 | 5/2006 | Moll et al. |
| 2006/0161136 A1 | 7/2006 | Anderson et al. |
| 2006/0161137 A1 | 7/2006 | Orban et al. |
| 2006/0161138 A1 | 7/2006 | Orban et al. |
| 2006/0167441 A1 | 7/2006 | Wang et al. |
| 2006/0178559 A1 | 8/2006 | Kumar et al. |
| 2006/0229587 A1 | 10/2006 | Beyar |
| 2006/0235436 A1 | 10/2006 | Anderson et al. |
| 2006/0270915 A1 | 11/2006 | Ritter et al. |
| 2006/0293643 A1 | 12/2006 | Wallace et al. |
| 2007/0012135 A1 | 1/2007 | Tierney et al. |
| 2007/0016174 A1 | 1/2007 | Millman et al. |
| 2007/0019330 A1 | 1/2007 | Wolfersberger |
| 2007/0021776 A1 | 1/2007 | Jensen et al. |
| 2007/0043338 A1 | 2/2007 | Moll et al. |
| 2007/0043455 A1 | 2/2007 | Viswanathan et al. |
| 2007/0149946 A1 | 6/2007 | Viswanathan et al. |
| 2007/0233044 A1 | 10/2007 | Wallace et al. |
| 2007/0239172 A1 | 10/2007 | Lee et al. |
| 2007/0250073 A1 | 10/2007 | Brock et al. |
| 2007/0250074 A1 | 10/2007 | Brock et al. |
| 2007/0260115 A1 | 11/2007 | Brock et al. |
| 2007/0276423 A1 | 11/2007 | Green |
| 2007/0283263 A1 | 12/2007 | Zawde et al. |
| 2007/0299479 A1 | 12/2007 | Saksena |
| 2008/0009791 A1 | 1/2008 | Cohen et al. |
| 2008/0039869 A1 | 2/2008 | Mills et al. |
| 2008/0045892 A1 | 2/2008 | Ferry et al. |
| 2008/0059598 A1 | 3/2008 | Garibaldi et al. |
| 2008/0119824 A1 | 5/2008 | Weitzner et al. |
| 2008/0119872 A1 | 5/2008 | Brock et al. |
| 2008/0125793 A1 | 5/2008 | Brock et al. |
| 2008/0125794 A1 | 5/2008 | Brock et al. |
| 2008/0140087 A1 | 6/2008 | Barbagli |
| 2008/0147091 A1 | 6/2008 | Cooper |
| 2008/0183136 A1 | 7/2008 | Lenker et al. |
| 2008/0215065 A1 | 9/2008 | Wang et al. |
| 2008/0245946 A1 | 10/2008 | Yu |
| 2008/0249536 A1 | 10/2008 | Stahler et al. |
| 2008/0300592 A1 | 12/2008 | Weitzner et al. |
| 2009/0012533 A1 | 1/2009 | Barbagli et al. |
| 2009/0082722 A1 | 3/2009 | Munger et al. |
| 2009/0105639 A1 | 4/2009 | Weitzner et al. |
| 2009/0105645 A1 | 4/2009 | Kidd et al. |
| 2009/0248043 A1 | 10/2009 | Tierney et al. |
| 2010/0010475 A1 | 1/2010 | Teirstein et al. |
| 2010/0256558 A1 | 10/2010 | Olson et al. |
| 2011/0077590 A1 | 3/2011 | Plicchi et al. |
| 2012/0182134 A1 | 7/2012 | Doyle |
| 2012/0184955 A1 | 7/2012 | Pivotto et al. |
| 2012/0197182 A1 | 8/2012 | Millman et al. |
| 2012/0220931 A1 | 8/2012 | Cohen et al. |
| 2013/0138118 A1 | 5/2013 | Doyle |

(56) References Cited

U.S. PATENT DOCUMENTS

2013/0321262 A1* 12/2013 Schecter ................ G06F 3/041
  345/156
2014/0371742 A1* 12/2014 Fruehauf ............ A61B 18/1492
  606/41

FOREIGN PATENT DOCUMENTS

WO    2007008967 A2    1/2007
WO    2009092059 A2    7/2009

OTHER PUBLICATIONS

State Intellectual Property Office of the People's Republic of China, First Office Action, Oct. 30, 2009, Chinese Patent Application 200680025512.7, "Remotely Controlled Catheter Insertion System," with English translation, (24 pgs. total).

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

International Preliminary Report on Patentability, Intl Application PCT/US2009/031357. International Bureau of WIPO, Jul. 29, 2010.

International Search Report and Written Opinion, Intl Application PCT/US2009/031357. International Search Authority, U.S. Patent and Trademark Office (ISA/US), Mar. 19, 2009.

U.S. Appl. No. 13/051,736, Final Office Action dated Nov. 5, 2012.

Hein et al., "Robot Supported Insertion of Catheters for Hyperthermia and Branch Therapy," Computer Assisted Radiology and Surgery, 1998, pp. 660-663.

Macoviak, "Catheter System for Surgical Access and Circulatory Support of the Heart," USPTO, Official Gazette, vol. 1278, Jan. 6, 2004.

U.S. Appl. No. 13/051,736, Non-Final Office Action dated Jul. 17, 2012.

U.S. Appl. No. 12/903,397, Non-Final Office Action dated Nov. 19, 2012.

Canadian Application 2,646,846, Office Action dated Sep. 19, 2012.

Extended European Search Report of Apr. 17, 2013; European Application No. 09702983.9.

Japanese Patent Application No. 2010-543298; Office Action of Mar. 19, 2013.

U.S. Appl. No. 13/461,463, Final Office Action dated Jun. 27, 2014.

U.S. Appl. No. 13/461,463, Non-Final Office Action dated Oct. 31, 2014.

U.S. Appl. No. 12/515,005, Non-Final Office Action dated Apr. 11, 2013.

U.S. Appl. No. 13/078,663, Non-Final Office Action dated Aug. 14, 2014.

* cited by examiner

SINGLE HAND OPERATED REMOTE CONTROLLER FOR REMOTE CATHETER POSITIONING SYSTEM

CROSS REFERENCE TO RELATED APPLICATIONS

The present invention claims the benefit of priority to U.S. Provisional Patent Application No. 61/874,434, entitled "SINGLE HAND OPERATION REMOTE CONTROLLER FOR REMOTE CATHETER POSITIONING SYSTEM," filed Sep. 6, 2013, the entire contents of which are incorporated herein by reference.

BACKGROUND

Many invasive medical procedures require the use of radiation to visualize and track the location of an inserted device. For example, procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system.

High dosages of radiation may have long term adverse health effects. A patient may be directly exposed only once or twice to radiation during such procedures and avoid such adverse effects. However, physicians, medical technicians, and staff may experience a large cumulative radiation dosage over time, both directly and indirectly, from conducting many procedures.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury.

SUMMARY OF THE INVENTION

The systems, methods, and devices of the various embodiments provide a remote controller for a catheter positioning system configured to be operated with a single hand by a catheter positioning system operator. In an embodiment, the remote controller may include a thumb joystick control, first wheel control, and second wheel control. In an embodiment, the remote controller may include various visual indicators and/or haptic feedback mechanisms providing information to a catheter positioning system operator.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

The systems, methods, and devices of the various embodiments provide a remote controller for a catheter positioning system configured to be operated with a single hand by a catheter positioning system operator. In an embodiment, the remote controller may include a thumb joystick control, first wheel control, and second wheel control. In an embodiment, the remote controller may include various visual indicators and/or haptic feedback mechanisms providing information to a catheter positioning system operator regarding an orientation and status of a catheter being positioned by a catheter positioning system.

Figure 1:
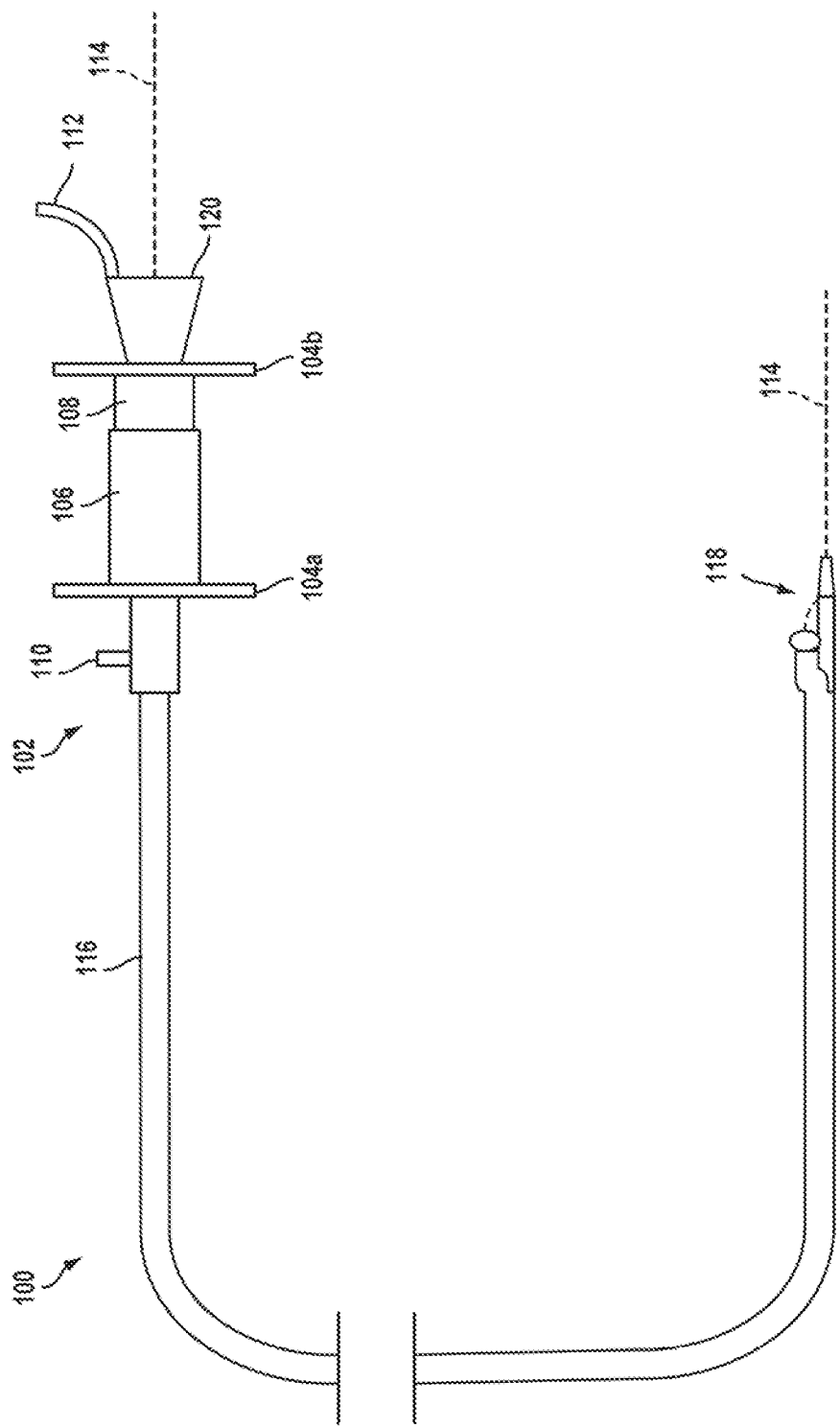
FIG. 1 is a diagram illustrating a top view of a catheter which could be used in accordance with various embodiments.

FIG. 1 illustrates an example catheter 100 that may be used in various embodiments. The catheter 100 may include a handle portion 102 and tube portion 116 and a tip portion 118. The handle portion 102 may be located at a proximal end of the catheter 100 while the distal end of the tube portion 116 may be inserted into the body of a patient.

The handle portion 102 of the catheter 100 may also include an irrigation port 110, which may be used to introduce water or other fluids to lubricate the catheter and ease insertion or retraction into the patient. The handle portion 102 may also include a back port 120 through which one or more wires or cables 112 may leave the handle portion 102. Cables 112 may supply power to the catheter 100 or transmit signals, such as sending commands from a remote controller or other control device to the catheter or relaying data from one or more transducers present on the catheter.

The handle portion 102 may include actuators to control the behavior of the catheter 100. For example, the handle portion 102 shown in FIG. 1 includes a front flange 104a and rear flange 104b that may be squeezed together such that the inner cylinder 108 slides inside the outer cylinder 106. This motion may actuate one or more mechanism at the tip 118 of the catheter. The catheter 100 may also be rotated about an axis 114, such as by applying a rotational force on the flanges 104a and 104b or other components of the catheter 100 that will cause rotation of the tip 118 of the catheter.

While the axis 114 illustrated in FIG. 1 is generally linear, it may conform to various curves of the tube portion 116 into which a catheter may be inserted.

The catheters described herein are presented merely as examples of catheters which may be suitable for use with the various embodiments. In the various embodiments, any type of catheter may be used. For example, the various embodiments may be applicable to catheters with different actuators or functions, such as actuators for deflecting the tip of the catheter to ease navigation inside a patient and/or for controlling one or more transducers at the tip (e.g., electrical leads, one or more sensor devices, ultrasound devices, etc.).

Figure 2:
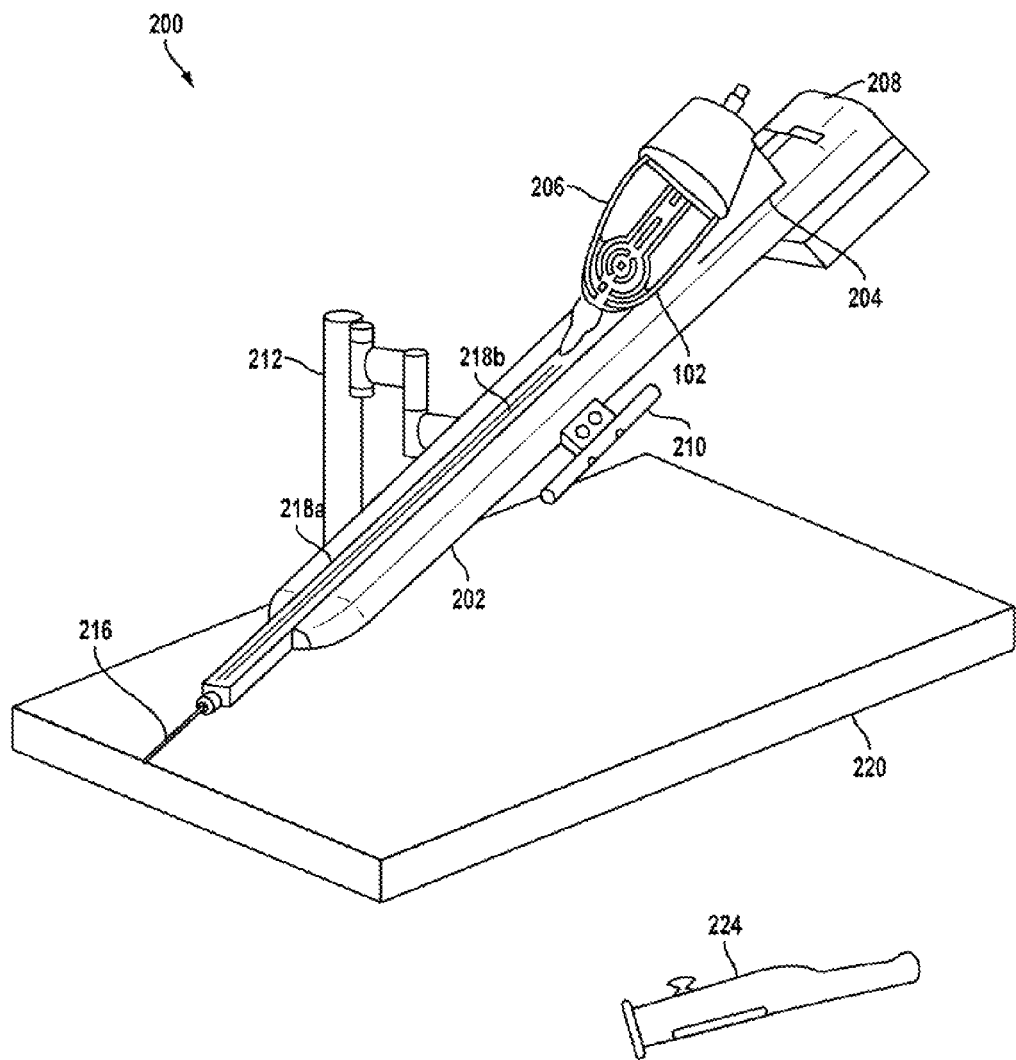
FIG. 2 is a diagram illustrating an oblique view of a remotely controlled catheter positioning device suitable for use with various embodiments.

FIG. 2 illustrates an embodiment catheter positioning device 200 with a remote controller 224. The catheter positioning device 200 may include a sled base 202 coupled with a sled member 204. The sled base 202 may be configured to advance the sled member 204 along the sled base 202 towards the body of the patient or back away from the patient. For example, the sled member may be moved with a motor 208 at one end of the sled base 202. The sled member 204 may move along a rail or other track, which may be configured with a driving mechanism such as a worm drive, back and forth along the longitudinal axis of the sled base 202.

The sled base 202 may be mounted with an arm 212, which may be configured with articulating joints and arms to position the sled base 202 over a surface, such as over an operating table 220. The arm 212 may be extended or rotated to position the sled base 202 relative to a patient on the operating table 220. The sled base 202 may include a handle 210 to move the sled base 202 into position. The sled base may also include a nose cone 216 that may be inserted into a patient. Alternately, the nose cone 216 may connect with an introducer or sheath that may be inserted into the patient. A catheter may be advanced along the sled base 202 and through the nose cone 216 into the patient.

The sled base 202 may include a sterile barrier in the form of a re-sealable delivery channel 218a to protect and guide the catheter along the sled base as it is advanced by the sled member 204. For example, the catheter may be coupled to the catheter handle 102 and may be inserted into the delivery channel 218a. The catheter handle 102 may be connected to the sled member 204 (such as by using the modular plate 206 discussed below) such that the catheter is driven forward by translation of the sled member 204 along the re-sealable delivery channel 218 in the sled base 202 and through the nose cone 216 into the patient.

The re-sealable delivery channel 218a may be flexible to allow the catheter to be inserted and removed repeatedly. For example, the re-sealable delivery channel may have a resealing groove 218b, such as with flexible plastic lips running along the top of the delivery channel 218a along the longitudinal axis of the sled base 202. The catheter may be pushed through the resealing groove 218b to position it inside the re-sealable delivery channel 218a (i.e., the plastic lips may separate to let the catheter pass then come back together to seal behind the catheter). The catheter may be removed by pulling the catheter back through the flexible plastic lips of the resealing groove 218b. While the re-sealable delivery channel 218a is described herein as being re-sealable, in some embodiments the re-sealable deliver channel 218a may be configured such that it is does not form a full seal, but merely closes enough to hold a catheter or a sheath within the channel to prevent buckling when the catheter is advanced towards/in the patient.

The sled member 204 may be coupled with a modular plate 206 to which a catheter handle 102 may be attached. Various embodiments of the modular plate 206 may accommodate many alternate catheter and catheter handle and/or control mechanisms with a corresponding modular plate 206 that may be used so that the catheter positioning system can accommodate many different types of catheters. Depending on the kind of catheter that is desired for a procedure, an appropriate modular plate 206 may be attached to the sled member 204 and the catheter may be attached to the module plate 206. The modular plate 206 may also integrate with any actuators on the catheter handle 102 thereby allowing an operator to control the actuators via the remote controller 224.

The sled member 204 may be configured to rotate the modular plate 206, thereby rotating a catheter connected to the modular plate 206. The sled member 204 may be configured to drive a rotation of the modular plate 206, or may be configured to rotate together with the modular plate 206. The rotation may be controlled remotely via the remote controller 224. By controlling translation along the sled base 202, the rotation of the sled member 204 and the modular plate 206, and the actuation of the catheter's handle via the modular plate 206, an operator may position or use the catheter in any way necessary for a desired operation. Further, an operator may control each of these degrees of freedom (e.g., translation, rotation, actuation, etc.) remotely with the remote controller 224.

Figure 3:
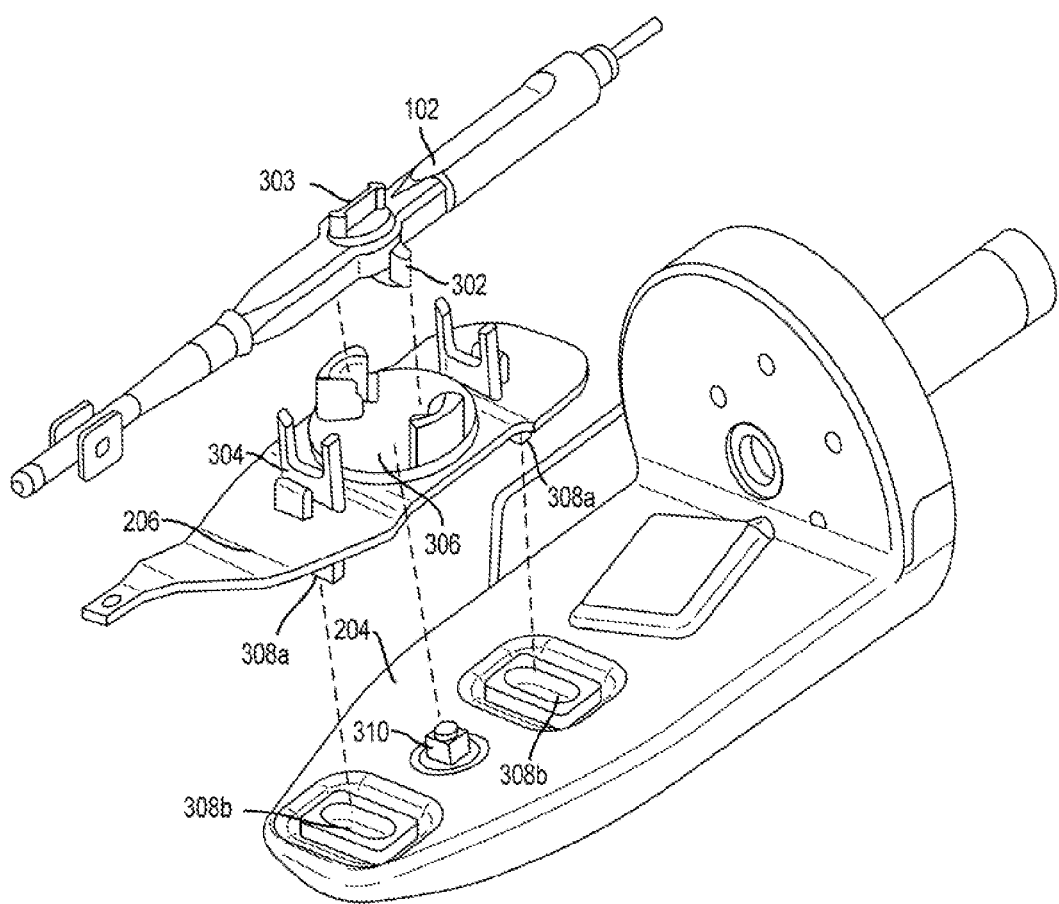
FIG. 3 is a diagram illustrating an exploded view of a catheter handle portion, a modular plate, and a sled member according to various embodiments.

FIG. 3 illustrates an exploded view of a catheter handle 102, modular plate 206, and sled member 204. The catheter handle 102 may include one or more actuators 302. The catheter handle 102 may further include a rotatable lever 303 as opposed to the flanges 104a and 104b shown in FIG. 1 to extend and retract the catheter. As discussed above, a different version of the modular plate 206 may be used so that various catheters with different actuators may be connected to the catheter positioning device. FIG. 3 illustrates a modular plate 206 that includes clamps 304 to secure the catheter handle 102 as well as a molded nest 306 configured to interface with the actuator 302 (i.e., the rotatable lever 303 may be controlled by rotating the molded nest 306, which may interact with the actuators 302).

The modular plate 206 may be rigidly connected to the sled member 204 such that translation or rotation of the sled member is transferred through the modular plate 204 to the catheter handle 102 to drive and position the catheter in rotational or linearly translational movement. The sled member 204 and modular plate 206 may be connected by one or more detachable joints having a connection mechanism, such as a socket 308b that receives a tab 308a of the modular plate 204. The sled member 204 may also include a control mechanism 310 to interface with the modular plate 206. The control mechanism 310 may allow the operator to control the catheter's actuators 302, such as by controlling the molded nest 306. in embodiments, the control mechanism 310 and the molded nest may be configured with a universal adapter such that the control mechanism may interface with any of the various modular plates 206 designed to connect with different catheter handles.

Figure 4:
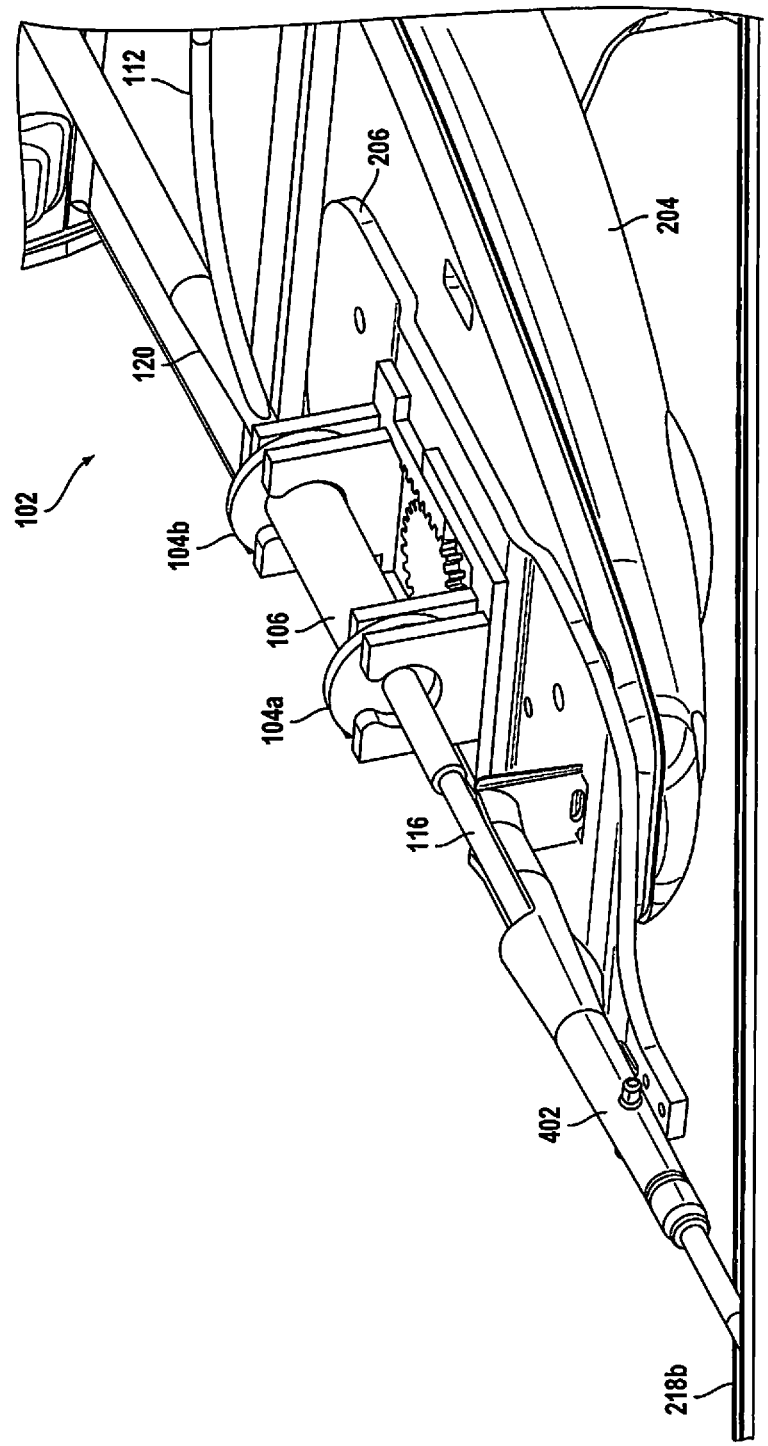
FIG. 4 is a diagram illustrating an oblique view of a catheter handle portion, a modular plate, and a sled member coupled together according to various embodiments.

FIG. 4 illustrates a view of a catheter handle 102 connected with the modular plate 206 and sled member 204. FIG. 4 illustrates a spreader 402, which may facilitate the insertion of the catheter tube 116 into the resealing groove 218b of the re-sealable delivery channel 218a. As shown in FIG. 4, the spreader 402 may be attached to the modular plate 206 and configured to lead the catheter's tube portion 116 into the resealing groove 218b of the re-sealable delivery channel 218a. As the sled member 204 is advanced, the end of the spreader 402 may stay inside the resealing groove 218*b* of the re-sealable delivery channel 218*a* by moving between the plastic lips of the resealing groove 218*b*. The lips of the resealing groove 218*b* may remain sealed over the re-sealable delivery channel 218*a* and around the spreader 402 where it is inserted. As the spreader 402 moves in a direction along the re-sealable delivery channel 218*a*, the lips of the resealing groove 218*b* may open about the spreader 402 and reseal behind the spreader 402 providing a movable closure around the spreader 402.

Figure 5:
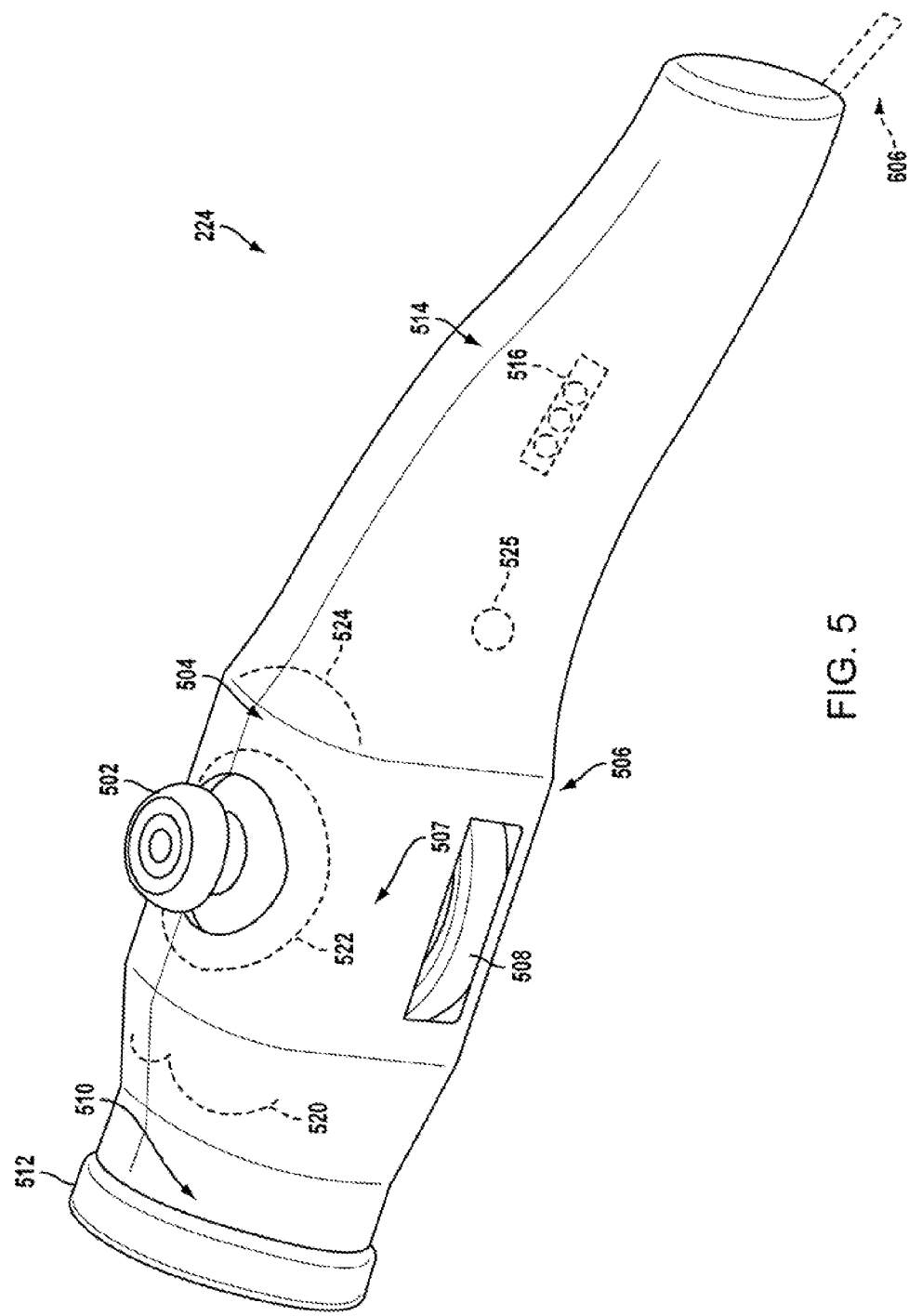
FIG. 5 is a diagram illustrating a perspective side view of a remote controller according to an embodiment.

FIG. 5 illustrates an embodiment remote controller 224 from a side perspective view. In an embodiment, the remote controller 224 may be configured to enable a catheter positing system operator to control the operation of the catheter positing system with one hand using the remote controller 224. The operator may manipulate the remote controller 224 in a manner similar to the manner in which the operator would manipulate the catheter in a manual catheterization procedure, e.g. without the remote positioning system. In an embodiment, surfaces, contours and control locations of the remote controller 224 may be formed ergonomically. For example the remote controller 224 may be formed, such as with a handle on a back side 514 of the body of the remote controller 224. The shape of the back side 514 may be configured to enable the remote controller 224 to be easily held in one hand. The remote controller 224 may include various controls, such as a thumb joystick control 502, a first wheel control 508, and a second wheel control 512 disposed on various portions of the body of remoter controller 224. In other embodiments, additional aspects of the remote controller 224, such as the size, the balance, the surface texture, the surface adhesion (e.g., stickiness), the grip contour, and so on, may be configured for a more positive control feel for the remote controller 224.

In an embodiment, the thumb joystick control 502 may extend from a surface 504 of the body of the remote controller 224 along a first axis. For example, the thumb joystick control 502 may extend from a top surface of the remote controller 224 in a manner configured to be similar to a top surface of a catheter handle. The thumb joystick control 502 may be any type control, such as an analog or digital joystick, with four or more axis of control. In an embodiment, forward deflection of the thumb joystick control 502 toward a front side 510 of the thumb joystick control 502 may control the in or forward motion (e.g., extension) of a catheter, such as to slide the sled member 204 down the sled base 202. A backward deflection of the thumb joystick control 502 toward a back side 514 of the remote controller 224 may control the out or backward motion (e.g., retraction) of the catheter, such as to slide the sled member 204 up the sled base 202. In an embodiment, left deflection of the thumb joystick control 502 toward a left side 507 of the thumb joystick control 502 may rotate the sled member 204 in a first direction, and right deflection of the thumb joystick control 502 toward a right side of the thumb joystick control 502 may rotate the sled member 204 in a second direction, such as opposite the first direction. In an embodiment, other axis of control and/or other functionality of the thumb joystick control 502, such as push button functionality, may be used to control additional actuator elements on a catheter installed on the catheter positioning system. For example, pushing down on the thumb joystick control 502 may activate an irrigation function, a lighting function or other function. In a further embodiment, the thumb joystick control 502 may be used as a momentary four-way switch. For example, deflections of the thumb joystick control 502 in the front, rear, left side and right side may each activate a separate momentary switch. Alternatively, the same momentary switch may be activated with different inputs and outputs depending on the direction of deflection. In some embodiments, the momentary switch may be a one shot switch that momentarily opens and closes for a fixed duration upon deflection. In other embodiments, the momentary switch may open (or close) for the duration of the deflection. In an optional embodiment, the remote controller 224 may include a selector switch 516, such as a three position switch, which may be configured to send signals for selecting the features of the catheter positioning system that inputs to the thumb joystick control 502 may control. As an example, the selector switch 516 may control whether deflection of the thumb joystick control 502 controls linear and rotary motions of the catheter only, sheath only, or both the catheter and sheath together, whether deflection of the thumb joystick control 502 activates a momentary switch or switches, and so on.

In an embodiment, the first wheel control 508 may be located on the remote controller 224 below the thumb joystick control 502. In an embodiment, the first wheel control 508 may be located near a bottom side 506 of the body of the remote controller 224. The first wheel control 508 may be a horizontal wheel rotating about a second axis, which may be a vertical axis with respect to a natural orientation of the remote controller (e.g., when held by an operator), such as an axis running from the bottom side 506 to the top side 504 of the remote controller 224. In an embodiment, the first wheel control 508 may be housed within the body of the remote controller 224 and a first portion of the first wheel control 508 may extend out past a left side 507 and second portion may extend out past a right side of the remote controller 224. In an embodiment, the first wheel control 508 may be any type control, such as an analog or digital control, for example a wheel coupled to a rotary encoder. In an embodiment, rotation of the first wheel control 508 may be used to generate signal sent to the catheter positioning system to steer a catheter having tip steering capability, such as turning the catheter tip left and/or right from a centered/straight orientation. For example, rotation of the first wheel control 508 may cause the remote controller 224 to send signals to the catheter positioning system to cause a rotation of a molded nest actuator interface on the modular plate 306 (e.g., FIG. 3) to rotate a catheter handle's actuator that will result in deflection of a distal tip of the catheter. In an embodiment, the first axis of the thumb joystick control 502 and the second axis of the first wheel control 508 may be coaxial (i.e., aligned with each other such that the first wheel control is below the thumb joystick control on the remote controller). In another embodiment, the first axis of the thumb joystick control 502 and the second axis of the first wheel control 508 may be parallel but offset from one another.

In an embodiment, the second wheel control 512 may be located on a distal end of the remote controller 224, such as the front end 510 of the body of the remote controller 224. The second wheel control 512 may be a vertical wheel rotating about a third axis, such as a horizontal axis running from the front side 510 of the remote controller 224 to the back side 514 of the remote controller 224. In an embodiment, the second wheel control 512 may be any type of control, such as an analog or digital control, for example a wheel coupled to a rotary encoder. In an embodiment, rotation of the second wheel control 512 may cause the remote controller 224 to send signals to the catheter positioning system to cause movement of an actuator interface that turns an actuator on the catheter handle to adjust the diameter of a loop (or other shape change feature) on the distal tip of the catheter. As an example, rotating the second wheel control 512 may cause the remote controller 224 to send signals to the catheter positioning system to cause it to move an actuator interface that turns an actuator on the catheter handle to adjust a loop diameter of a loop style diagnostic catheter. In some implementations, depending on the catheter type and user preferences, the functionality of the thumb joystick control 502, the first wheel control 508 and the second wheel control 512 may control the same catheter positioning actions. In some implementations, the first wheel control 508 and the second wheel control 512 may provide the same level of control as the thumb joystick control 502. In other implementations, the first wheel control 508 and the second wheel control 512 may provide a coarse adjustment of the control actions and the thumb joystick control 502 may provide finer adjustments of the control actions. Alternatively or additionally, the first wheel control 508 and the second wheel control 512 may allow control actions to be conducted when the thumb joystick control 502 is being used for other actions such as a four way switch, or momentary switch as described herein.

In an optional embodiment, the remote controller 224 may include one or more optional indicators 520, 522, 524 which may visually indicate information. In an embodiment, additional optional indicators may be included on the remote controller 224. For example, additional lights may indicate whether the remote controller 224 is controlling the catheter, the sheath, or both the catheter and the sheath. In another embodiment, the remote controller 224 may illuminate to visually indicate information and the intensity and/or color of the illumination may be adjusted to indicate additional information. In an optional embodiment, the remote controller 224 may provide haptic feedback to a user. For example, the remote controller 224 may include a vibratory motor configured to cause the remote controller 224 to vibrate in the hand of a user to provide information to the user. As another example, the thumb joy stick control 502, first wheel control 508, and/or second wheel control 512 may be configured to provide information to a user of the remote controller 224 by increasing and/or decreasing a resistance to motion of the thumb joy stick control 502, first wheel control 508, and/or second wheel control 512 by a user. As a further example, one or more of the thumb joy stick control 502, first wheel control 508, and/or second wheel control 512 may be configured with physical stops to prevent further movement of the thumb joy stick control 502, first wheel control 508, and/or second wheel control 512 when a limit of motion (e.g., a maximum rotation, a maximum deflection, a maximum extension, a maximum retraction, etc.) of the catheter and/or catheter positioning system is reached.

In an optional embodiment, the remote controller 224 may include a kill switch 525 used to determine whether the remote controller 224 is being held by a user. As an example, the kill switch 525 may be an infrared switch that enables operation of the remote controller 224 by sensing heat from the hand of the operator when held. The kill switch 525 may further cause the remote controller 224 to signal the remote catheter positioning system (e.g., a control computer coupled to the positioning system) when the remote controller 224 is being held by a user. Still further, the kill switch 525 may disable the remoter controller 224 or signal the remote catheter positioning system when detecting that the remote controller 224 is not being held. Other examples of kill switches 525 may include spring loaded buttons, light sensing switches, capacitive switches, etc.

Figure 6:
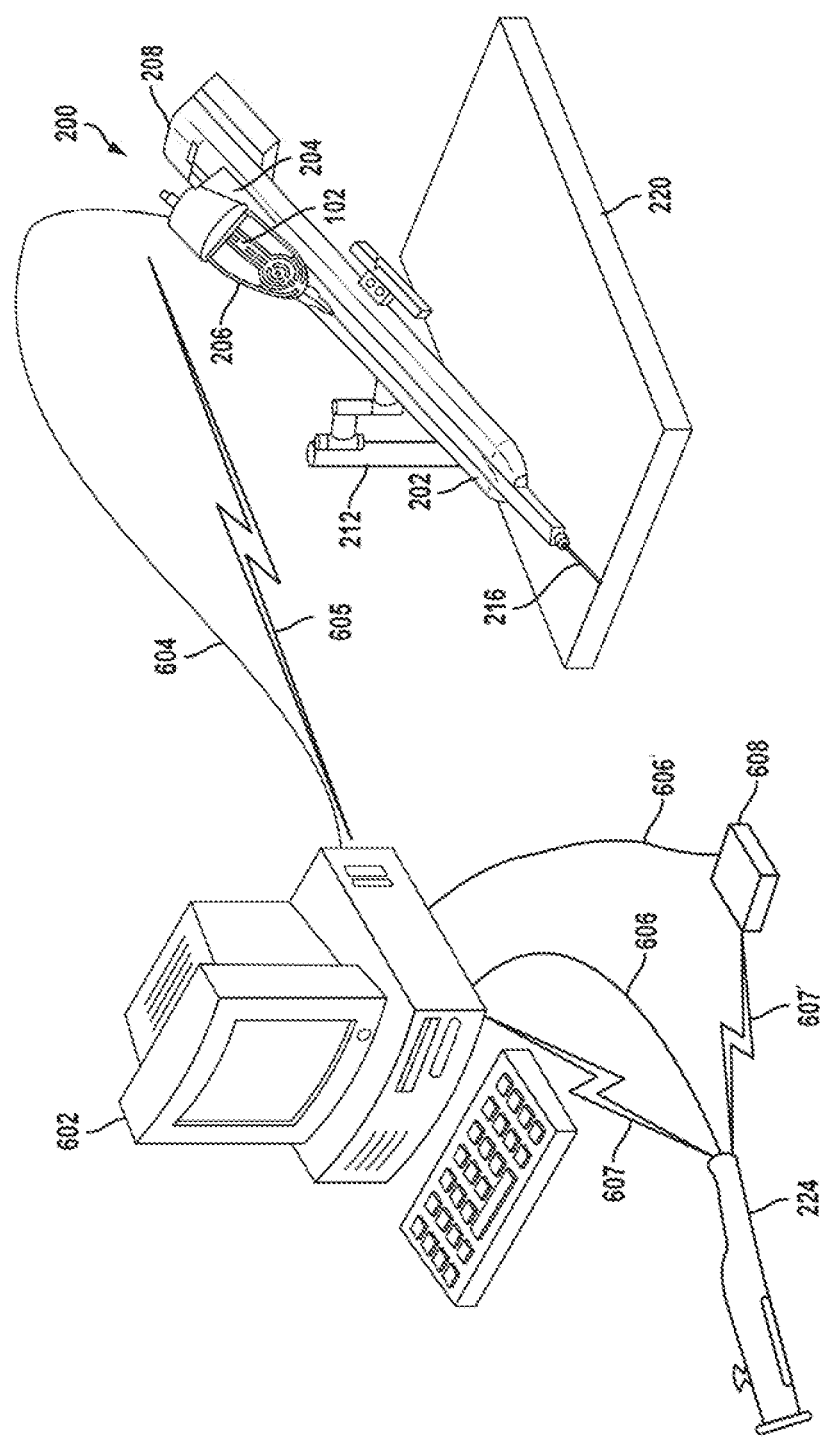
FIG. 6 is a system diagram illustrating an embodiment remote controller, a remotely controlled catheter system, and a programmable control system.

The remote controller 224 may be configured to communicate control signals to a control computer or other devices of the catheter positioning system via a wired 606, 606' or wireless data link 607, 607' as illustrated in FIG. 6. A remote controller 224 may be connected to the by a wired connector 606 or a wireless data link 607. The programmable control system 602 may also be connected to the catheter positioning device 200 by a wired connector 604 or a wireless data link 605.

In an embodiment, the remote controller 224 may be configured to communicate control signals to a programmable control system 602 or other control devices of the catheter positioning system 200 via a wireless data link 607, such as a Bluetooth® link, a Wi-Fi® link, an infrared data link, etc. This embodiment may enable the clinician to manipulate the handle to better control the catheter positioning system 200 unimpeded by a control cable.

In another embodiment, the remote controller 224 may be configured to communicate control signals to a control computer or other devices of the catheter positioning system via an optical fiber or electrical cable 606. This embodiment may reduce the chance of wireless control signals interfering with medical equipment (e.g., electrophysiology catheters).

In a further embodiment, the remote controller 224 may be configured to communicate control signals via a wireless data link 607' (e.g., a Bluetooth® link, a Wi-Fi® link, an infrared data link, etc.) to a receiver device 608, which may be positioned near the clinician behind shielding and configured to receive and relay those signals to a control computer or other devices of the catheter positioning system via an optical fiber or electrical cable 606'. This embodiment may combine the manipulation advantages of a wireless controller with reduced signal emissions within the operating room enabled by a wired or fiber optic control cable.

The various wireless data links described herein, such as wireless data links 605, 607 and 607' may be established using any wireless communication protocol (e.g., Bluetooth®, Wi-Fi®, etc.). In an embodiment, the wireless data links may be established using a secure communication protocol ensuring that only communications from authorized devices are accepted over the wireless data link.

The programmable control system 602 may output command signals to the catheter positioning system 200 based on or in response to signals received from the remote controller 224. Additionally, the programmable control system 602 may be programmed based on signals received from the remote controller 224 to issue a sequence of command signals to the catheter positioning system 200, such as through a calibration, training or programming operation. In such a calibration, training or programming operation, a clinician may manipulate the programmable control system 602 so as to cause the catheter positioning system 200 to advance, rotate and manipulate a catheter in a desired manner, and the control sequence may be stored in memory of the programmable control system 602. Such system training may be accomplished by recording command signals (e.g., signals received from the remote controller 224 or issued by the programmable control system 602) during an actual operation (essentially remembering the procedure), or in a dedicated training session in which the system is programmed without a patient present. For example, a user may train the programmable control system to direct the positioning system to execute a series of translation and rotation movements by manipulating the control inputs on the remote controller 224 as if directing the movements in real time. Programmed movements of the positioning device may also be input or supplemented by entering commands into a keyboard. The programmable control system 602 may store the command inputs and then combine the commands into a single programmed movement, such as in response to an operator selecting a number of pre-trained/programmed movements that should be accomplished in an indicated sequence. Programmed movements may include various combinations of the commands, such as simultaneously rotating and translating the system to create a "corkscrew" maneuver. These programmed movements may be triggered later by a single input, such as a user identifying the sequence by a file name or preset program and pressing an execute key on the controller or the system keyboard.

In an embodiment, the programmable control system 602 may store different user profiles for different users of the remote controller 224, such as in a storage device. The storage device may be a storage device associated with the programmable control system 602, may be memory of the remote controller 224, or a combination of storage locations. For example, various user settings and/or preferences for the remote controller 224 may be stored locally in a memory or storage device of the remote controller 224 and may be transferred to the programmable control system 602 to be stored in a memory or storage device, such as in association with a database of user settings. The user profiles may include user selected levels for configurable settings of the remote controller 224, such as sensitivities, friction, speed of rotation, speed of extension, speed of retraction, brightness of indicators, and resolution of various controls located on the remote controller, haptic feedback settings, etc. The programmable control system 602 may identify the current user of the remote controller 224, for example via a user log in, retrieve current the user's profile from a memory, and adjust the configurable settings to the selected levels indicated in the user profile. In this manner, configurable settings may be tailored to fit specific users of the remote controller 224.

Figure 7:
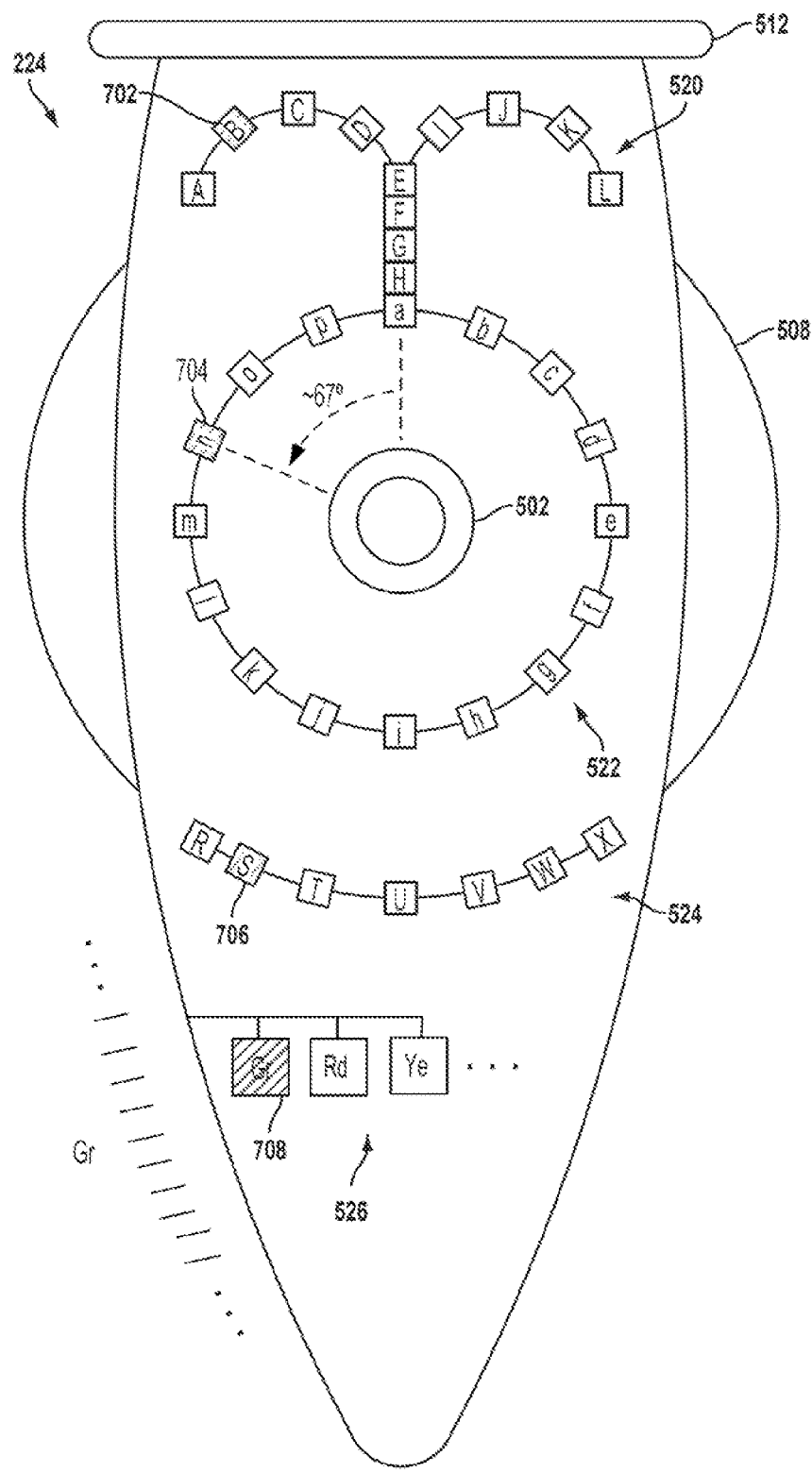
FIG. 7 is a diagram illustrating a top view of a remote controller according to an embodiment.

FIG. 7 illustrates three optional indicators or sets of indicators 520, 522, 524 that may be included in an embodiment of the remote controller 224. In an embodiment, each of the indicators 520, 522, 524 may be a series of lights arranged in patterns, such as a pattern of individual light emitting diodes (LEDs). In another embodiment, each of the indicators 520, 522, 524, may be a display (e.g., an LED screen) configured to display images representing a series of lights arranged in patterns. In an embodiment, the indicators 520, 522, 524 may work together and/or separately to communicate information regarding the orientation of a catheter and/or the catheter positioning system 200.

In an embodiment, a catheter tip orientation indicator 520 may be provided on the remote controller 224 in the form of a series of lights A, B, C, D, E, F, G, H, I, J, K, and L arranged along two curves representative of different degrees of tip bend that can be introduced in steerable catheters. The indicator 520 may also indicate a linear position, including a degree of insertion or retraction, such as through the illumination of lights E-H. By illuminating a correct one of the series of lights A, B, C, D, E, F, G, H, I, J, K, and L, the catheter tip orientation indicator 520 can inform a user of the catheter tip's current orientation/configuration. For example, the illuminated light 702 corresponding to light B shown in FIG. 7 may indicate that the tip of the catheter has been deflected (through articulation of the catheter control actuators by the catheter positioning system) to the left by three-fourths of its potential deflection. In the illustrated embodiment, when the catheter is fully deflected to the left the light A would illuminate and light B would be dim, providing an easy to understand indication that the catheter has reached its articulation limit. In this manner, the catheter tip orientation indicator 520 may inform the user whether the catheter tip is deflected, its direction, to the extent which it is deflected, including whether an articulation limit has been reached.

In an embodiment, a catheter rotation indicator 522 may be provided on the remote controller 224 in the form of a series of lights a, b, c, d, e, f, g, h, i, j, k, l, m, n, o, and p arranged in a circle or ellipse, such as a ring around the thumb joystick control 502. The catheter rotation indicator 522 may indicate the angle of rotation of the catheter with respect to the handle up orientation. For example, in FIG. 7 the "n" catheter rotation indicator light 704 is illuminated indicating that the current rotational orientation of the catheter is about 67 degrees to the left. As another example, when the catheter is oriented with the handle facing up, the "a" light would be illuminated. This embodiment provides the clinician with an intuitive indication of rotational orientation, since the clinician can hold the controller vertical to see orientation as it would appear on the machine.

The catheter positioning system 200 can rotate the catheter in either direction and can rotate the catheter several times about its long axis, which can present a problem in terms of twisted connectors and fluid-carrying tubing. Therefore, an embodiment may also include a rotation count indicator 524 provided on the remote controller 224 in the form of a series of lights R, S, T, U, V, W, and X, such as arranged in an arc. This embodiment provides an intuitive indication of the direction (i.e., left, right, clockwise or counterclockwise, etc.) and the number of rotations through which the catheter has been rotated. The combination of the catheter rotation indicator 522 and the rotation count indicator 524 may provide the clinician with a complete picture of the rotational orientation of the catheter. For example, in FIG. 7, the illumination of light S at 706 may indicate the catheter has been rotated two full turns to the left and the illumination of light "n" at 704 may indicate that the catheter has been rotated an additional 67 degrees. In other words, the illuminated lights at 704 and 706 indicates that the catheter has been rotated a total of about 787 decrees to the left. As a further example, when the catheter has not been rotated at all, the lights "a" and U would be illuminated. The rotation count indicator 524 may also indicate when catheter rotation limit has reached a limit, such as by illuminating lights R for maximum left rotations or light X for maximum right rotations.

In a further embodiment, additional visible indicators 526 to indicate an operation mode or orientation of the catheter positioning system may be included on or within the remote controller 224. Such indicators 526 may be in the form of different colors, such as green, red, or yellow. In an embodiment, the body of the remote controller 224 may be of a translucent material and an indicator may be different colored lights within the handle that illuminate to turn the handle particular colors to indicate different conditions, operation modes or states of the catheter positioning system. For example, a green light 708 in the interior of the handle may illuminate to turn the handle green when a catheter has been properly inserted in the system is ready for operation, and a red light in the interior of the handle may illuminate to turn the handle red when it is not safe to operate the system. Other indicators and/or color combinations may be used to communicate control modes, such as catheter only control, sheath only control, or both catheter and sheath control. Similarly, the illumination of visible indicators 526 may indicate whether a catheter and/or catheter dock is positioned correctly or incorrectly in the catheter positioning system.

Figure 8:
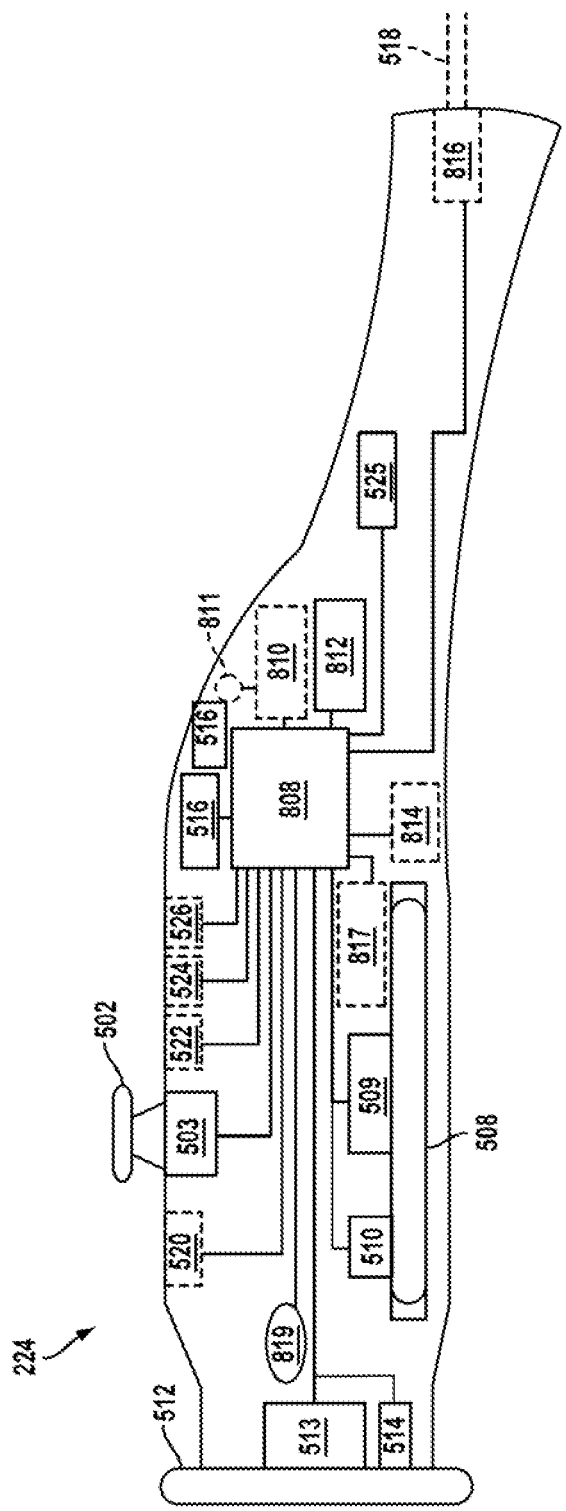
FIG. 8 is a component block diagram illustrating a remoter controller according to an embodiment.

FIG. 8 is a component block diagram of the remote controller 224 illustrating various component parts according to one or more embodiments. The remote controller 224 may include a thumb joystick control 502 coupled to a joystick digital encoder 503 connected to a processor 808. The remote controller 224 may include a first control wheel 508 coupled to a first rotational digital encoder 509 connected to the processor 808, and a second control wheel 512 coupled to a second rotational digital encoder 513 connected to the processor 808. The joystick digital encoder 503, first rotational digital encoder 509 and second rotational digital encoder 513 may generate signals indicating the position or movement their respective thumb joystick control 502, the first control wheel 508, and the second control wheel 512 (e.g., deflection angle, rotation, etc.), with such signals configured to interpretable by the processor 808.

In an embodiment, the thumb joystick control 502, the first control wheel 508, and/or the second control wheel 512 may include an actuator mechanism as part of or coupled to their respective digital encoder 509, 513 and additional haptic actuator mechanisms 510, 514 configured to provide haptic feedback, such as in the form of resistance to movement and/or vibration. The processor 808 may configured to send haptic feedback control signals to the actuators within the thumb joystick control 502, the first control wheel 508, and/or the second control wheel 512 to generate perceptible haptic feedback a clinician handling the remote controller 224, such as when a movement or actuation corresponding to the control input is nearing or has reached a limit. For example, when a catheter equipped with a tip pressure sensor (or tip bend sensor) sends signals indicating that the tip of the catheter is pressing against tissue (i.e., resisting further forward movement), such signals may be interpreted by the programmable control system 602, which may send control signals to the processor 808 of the remote controller 224, which in turn may control a haptic actuator mechanism 510, 514 to cause it to resist further actuation of its controller (e.g., the first control wheel 508). In this manner, the haptic feedback resistance on the controller wheel may simulate the tactile feel that the clinician would have when advancing the catheter manually. In an embodiment, the force of the haptic feedback resistance generated by any of the haptic actuator mechanisms 510, 514 in the remote controller 224 may be adjustable. The programmable control system 602 may identify the clinician operating the remote controller 224 and may send control signals to the processor 808 of the remote controller 224 indicating the level of haptic feedback resistance to generate for the clinician (for example, based on that clinician's user profile setting stored in a memory of the programmable control system 602). The processor 808 may in turn control a haptic actuator mechanism 510, 514 to cause it to resist further actuation of its controller with the level of haptic feedback resistance indicated in the received control signal. In this manner, the level of haptic feedback may be changed to fit a specific clinician and/or to increase or decrease a distraction factor caused by the haptic feedback.

The catheter tip orientation indicator 520, catheter rotation indicator 522, and rotation count indicator 524, and catheter status indicator 526, may be connected to and controlled by the processor 808 to display visual indications to the user of the remote controller 224 as described above. Also as described above, in an embodiment the remote controller 224 may include an internal illumination source 819, such as one or more LEDs, connected to the processor 808 and configured to illuminate the body of the remote controller 224 in one or more colors. In an embodiment, the body of the remote controller 224 may be translucent or semi-transparent such that the illumination source 819 may cause the body of the remote controller to appear to glow when illuminated.

In an embodiment, a kill switch 525 may be connected to the processor 808 and configured to sense when the remote controller 224 is being held by a user. In an embodiment, the processor 808 may be configured with processor executable instructions to determine a status of the kill switch 525 before performing operations to send control indications. In an alternative embodiment, the processor 808 may be configured to send signals to the programmable control system 602 indicating when the remote controller 224 is being held by a user (or not) and the control system may be configured to limit or prevent remote operation of the catheter positioning system when such signals indicate the remote controller is not being held.

In an optional embodiment, the remote controller 224 may include a vibratory motor 817 connected to the processor 808 and configured to vibrate the remote controller 224 in order to provide haptic feedback to a clinician holding the remote controller 224. Such vibrating haptic feedback may be used to inform the clinician that a safety limit or threshold has been reached or an undesirable condition may result from further actuation.

In an embodiment, the remote controller 224 may include a switch 516 connected to the processor 808 that is configured to control an operating mode of a catheter positioning system. For example, the switch 516 may be a multi-position switch to enable the clinician to select from a number of operating modes, such as a safe mode, automatic withdraw mode, an operate mode and a train mode.

In an embodiment, the remote controller 224 may include a battery 814 connected to the processor 808 and/or other elements of the remote controller 808 requiring power to operate. The battery 814 may be rechargeable, such as via an inductive charging circuit (not shown).

In an embodiment, the processor 808 may be connected to a memory 812 and to a transceiver 816 connected to a data communication cable 518 for coupling the remote controller 224 and processor 808 to the programmable control system 602 of a catheter positioning system. In an optional embodiment, the processor 808 may be connected to a wireless transceiver 810 connected to an antenna 811 for establishing a wireless data connection with the programmable control system 602 or an intermediary control signal relay 608.

Figure 9:
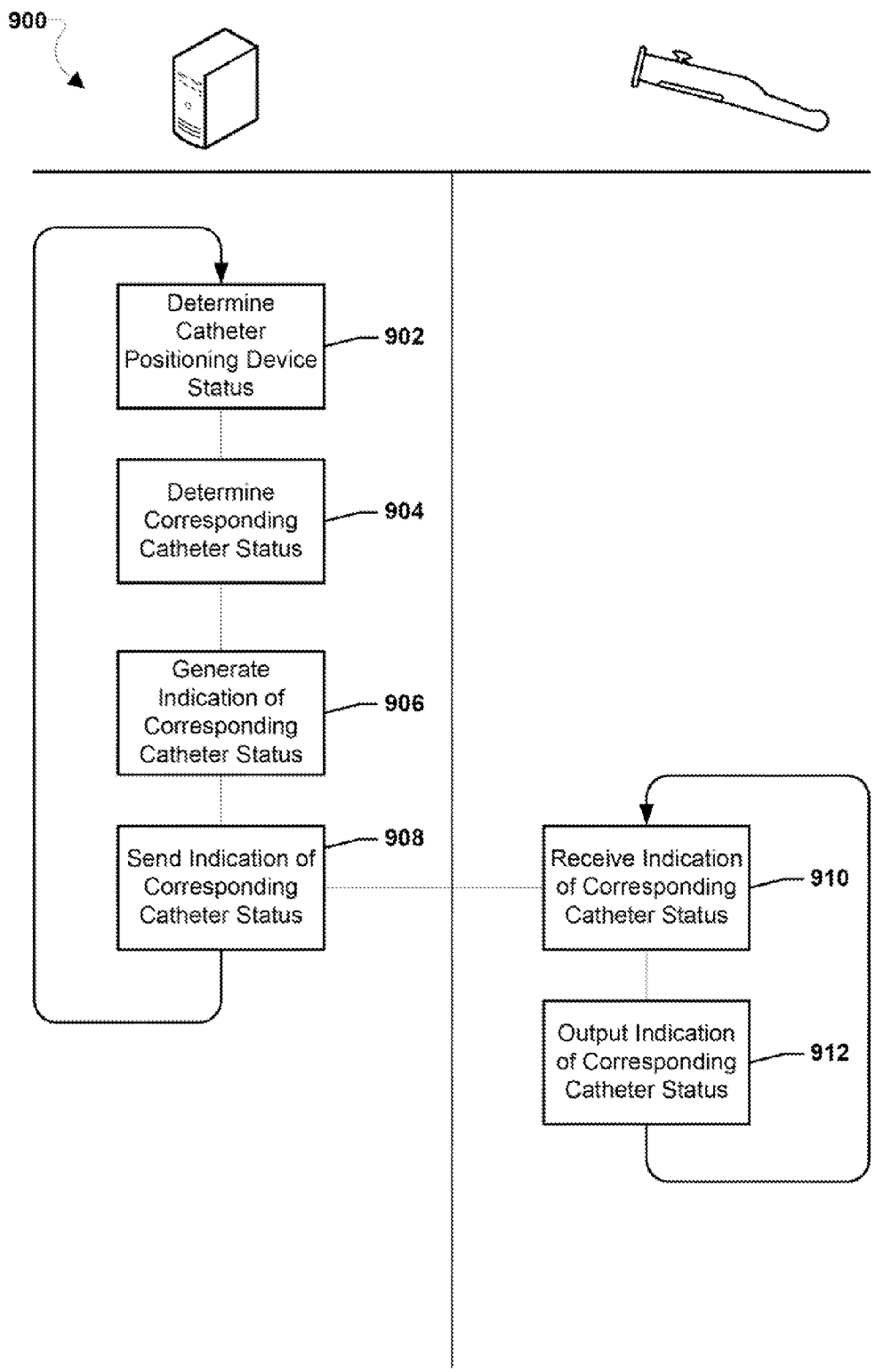
FIG. 9 is a process flow diagram illustrating an embodiment method for outputting an indication of a corresponding catheter status at a remote controller of a catheter positioning system

FIG. 9 illustrates an embodiment method 900 for outputting an indication of a corresponding catheter status at a remote controller of a catheter positioning system. In an embodiment, the operations of method 900 may be performed by a processor of a catheter positioning system (e.g., a processor within the programmable control system 602 described above with reference to FIG. 6) and a processor 808 of a remote controller. In block 902 the catheter positioning system processor may determine a catheter positioning device status. As examples, the catheter positioning system processor may determine a rotation status (e.g., number of rotations of a sled member of a catheter positioning device), extension status (e.g., distance down a track of a positioning device), molded nest status (e.g., position of a rotatable molded nest), etc. In block 904 the catheter positioning system processor may determine a corresponding catheter status. In this operation the catheter positioning system processor may reference a data table correlating catheter positioning device status information to catheter status information to determine a corresponding catheter status based on the determined catheter positioning device status. As an example, the catheter positioning system processor may use a data table of actuator characteristics to determine the actuator translation values for the particular catheter installed on the machine, and use the obtained actuator translation values to calculate a tip deflection of the catheter based on a measured angle or rotation (or number of rotations) of the catheter's tip-deflection actuator.

In block 906 the catheter positioning system processor may generate a control signal for activating a proper indication of the corresponding catheter status on a display or indicator on the remote controller. As an example, the catheter positioning system processor may generate a control signal for illuminating a proper light or lights of a display (e.g., one of displays 520, 522, 524, 526 described above) on the remote controller to indicate the determined catheter status to a user of the remote controller. As another example, the catheter positioning system processor may generate a control signal for activating a haptic actuator or vibration motor to provide haptic feedback to the user that the catheter has reached maximum deflection, such as by resisting movement of a thumb joy stick and/or control wheel. In block 908 the catheter positioning system processor may send the generated control signals to the remote controller and in block 910 the remote controller processor may receive the control signals. In block 912 the remote controller processor may activate the corresponding display or haptic actuator/motor to output the proper indication of the corresponding catheter status. As an example, the remote controller processor may illuminate lights of a display 520, 522, 524, or 526 on the remote controller to indicate the determined catheter status to a user of the remote controller. As another example, the remote controller processor may control a haptic actuator on the joy stick to stop/resist further movement of the thumb joy stick, thereby providing haptic feedback to the user that the catheter has reached a maximum deflection. The operations of method 900 may be performed continually by the catheter positioning system processor and remote controller processor to output indications of the catheter status.

Figure 10:
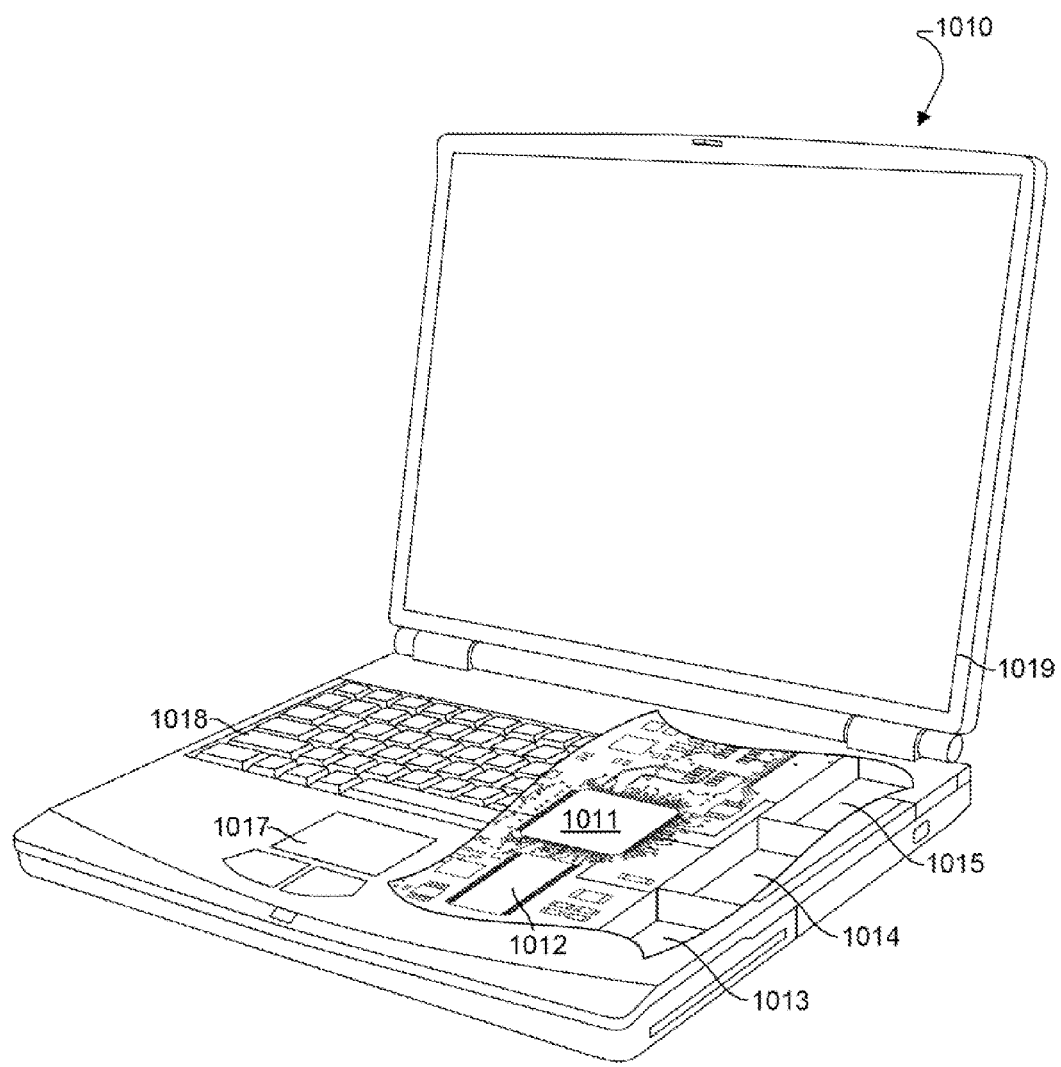
FIG. 10 is a component block diagram illustrating a programmable control system computer suitable for use with the various embodiments.

The various embodiments for interacting with an embodiment remote controller and a catheter positioning system described above may be implemented within a variety of programmable control system computers 1010, and example component block diagram of which is illustrated in FIG. 10. A programmable control system computer 1010 typically includes a processor 1011 coupled to volatile memory 1012 and a large capacity nonvolatile memory, such as a disk drive 1013 of Flash memory. The programmable control system computer 1010 may also include a floppy disc drive 1014 and a compact disc (CD) drive 1015 coupled to the processor 1011. The programmable control system computer 1010 may also include a number of connector ports coupled to the processor 1011 for establishing data connections to the remote controller and the catheter positioning system, and may be any form of connection such as a USB or FireWire® connector sockets. Ethernet sockets, or other network connection circuits for coupling the programmable control system computer 1010 to the catheter positioning system and/or a network. In a notebook configuration, the programmable control system computer 1010 housing includes the touchpad 1017, the keyboard 1018, and the display 1019 all coupled to the processor 1011. Other configurations of the programmable control system computer 1010 may include a computer mouse or trackball coupled to the processor (e.g., via a USB input) as are well known, which may also be use in conjunction with the various embodiments.

The processors 808 and 1011 may be any programmable microprocessor, microcomputer or multiple processor chip or chips that can be configured by software instructions (applications) to perform a variety of functions, including the functions of the various embodiments described above. In some devices, multiple processors may be provided, such as one processor dedicated to wireless communication functions and one processor dedicated to running other applications. Typically, software applications may be stored in the internal memory 812, 1012, 1013 before they are accessed and loaded into the processors 808 and 1011. The processors 808 and 1011 may include internal memory sufficient to store the application software instructions. In many devices the internal memory may be a volatile or nonvolatile memory, such as flash memory, or a mixture of both. For the purposes of this description, a general reference to memory refers to memory accessible by the processors 808 and 1011 including internal memory or removable memory plugged into the device and memory within the processor 808 and 1011 themselves.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A remote controller for a catheter positioning system, comprising:
   a body;
   a thumb joystick control extending from a surface of the body along a first axis;
   a first wheel control passing through the body and configured to rotate about a second axis of the remote controller, a first portion of the first wheel control extending from a first side of the body and a second portion of the first wheel control extending from a second side of the body opposite the first side;
   a second wheel control attached to a third side of the body and configured to rotate about a third axis of the remote controller, wherein the thumb joystick control, the first wheel control and the second wheel control are configured to control a position of a catheter tip, wherein the position comprises one or more of: a rotational position of the catheter tip, a linear position of the catheter tip, and a bending position of the catheter tip;
   a first indicator including a first series of lights arranged along two curves, the first indicator configured to generate a first indication of one or more of the bending position and the linear position of the catheter tip;
   a second indicator including a second series of lights arranged in a ring around the thumb joystick control, the second indicator configured to generate a second indication of the rotational position of the catheter tip;
   a third indicator including a third series of lights arranged in an arc, the third indicator configured to generate a third indication of a number of rotations of the catheter tip; and
   a processor connected to the thumb joystick, the first wheel control, the second wheel control, the first indicator, the second indicator, and the third indicator, wherein the processor is configured to with processor executable instructions to perform operations that activate one or more of the first indicator, the second indicator, or the third indicator based on a status of the catheter positioning system.

2. The remote controller of claim 1, wherein one or more of the thumb joystick control, the first wheel control, and the second wheel control are coupled to a haptic actuator configured to provide haptic feedback.

3. The remote controller of claim 2, wherein the haptic feedback comprises resisting movement of the one or more of the thumb joystick control, the first wheel control, and the second wheel control.

4. The remote controller claim 1, wherein the first axis of the thumb joystick control and the second axis of the first wheel control are approximately parallel but offset from one another.

5. The remote controller of claim 1, wherein:
   the first wheel control and the second wheel control are configured to provide coarse adjustments of the one or more of the rotational position, the linear position, and the bending position; and
   the thumb joystick control is configured to provide a fine adjustment of the one or more of the rotational position, the linear position, and the bending position.

6. The remote controller of claim 1, wherein:
   the thumb joystick control is configured as a four way switch; and
   the first wheel control and the second wheel control provide adjustments of one or more of the rotational position, the linear position, and the bending position.

7. The remote controller of claim 6, wherein the thumb joystick control is configured as a momentary switch.

8. The remote controller of claim 1, further comprising a storage device, wherein the processor is configured with the processor executable instructions to perform operations further comprising storing one or more user configurable settings.

9. The remote controller of claim 8, wherein the one or more user configurable settings comprises one or more of: a sensitivity, a friction, a speed of rotation, a speed of extension, a speed of retraction, a brightness, a haptic feedback and a resolution of one or more of the thumb joystick control, the first wheel control, the second wheel control, the first indicator, the second indicator, and the third indicator.

10. A remote controller for a catheter positioning system, comprising:
    a body that is semi-transparent;
    an illumination source within the body, wherein the illumination source is configured to illuminate the body;
    a thumb joystick control extending from a surface of the body along a first axis;

a first wheel control passing through the body and configured to rotate about a second axis of the remote controller, a first portion of the first wheel control extending from a first side of the body and a second portion of the first wheel control extending from a second side of the body opposite the first side;
a second wheel control attached to a third side of the body and configured to rotate about a third axis of the remote controller, wherein the thumb joystick control, the first wheel control and the second wheel control are configured to control a position of a catheter tip, wherein the position comprises one or more of: a rotational position of the catheter tip, a linear position of the catheter tip, and a bending position of the catheter tip;
a first indicator configured to generate a first indication of one or more of the bending position and the linear position of the catheter tip;
a second indicator configured to generate a second indication of the rotational position of the catheter tip;
a third indicator configured to generate a third indication of a number of rotations of the catheter tip; and
a processor connected to the illumination source, the thumb joystick, the first wheel control, the second wheel control, the first indicator, the second indicator, and the third indicator, wherein the processor is configured with processor executable instructions to perform operations comprising controlling the illumination source based on a status of the catheter positioning system.

11. A catheter positioning system, comprising:
a catheter positioning device;
a programmable control system coupled to the catheter positioning device; and
a remote controller comprising:
 a body;
 a thumb joystick control extending from a top side of the body;
 a first wheel control passing through the body and configured to rotate about a first axis of the remote controller, a first portion of the first wheel control extending from a first side of the body and a second portion of the first wheel control extending from a second side of the body opposite the first side;
 a second wheel control attached to a third side of the body and configured to rotate about a second axis of the remote controller, wherein the thumb joystick control, the first wheel control and the second wheel control are configured to control a position of a catheter tip;
 a first indicator including a first series of lights arranged along two curves, the first indicator configured to generate a first indication of one or more of a bending position and a linear position of the catheter tip;
 a second indicator including a second series of lights arranged in a ring around the thumb joystick control, the second indicator configured to generate a second indication of a rotational position of the catheter tip;
 a third indicator including a third series of lights arranged in an arc, the third indicator configured to generate a third indication of a number of rotations of the catheter tip;
 a remote controller processor coupled the thumb joystick control, the first wheel control, the second wheel control, the first indicator, the second indicator, and the third indicator; and
 a transceiver coupled to the remote controller processor and configured to transmit first signals from the remote controller processor to the programmable control system and provide second signals received from the programmable control system to the remote controller processor,
 wherein the remote controller processor is configured to receive user input via at least one of the thumb joystick control, first wheel control, and second wheel control and, in response to the received user input, to send commands via the transceiver to the programmable control system for controlling operations of the catheter positioning device to control the position of the catheter tip.

12. The catheter positioning system of claim 11, wherein one or more of the thumb joystick control, the first wheel control, and the second wheel control are coupled to a haptic actuator configured to provide haptic feedback.

13. The catheter positioning system of claim 12, wherein the haptic feedback comprises resisting movement of the one or more of the thumb joystick control, the first wheel control, and the second wheel control, and wherein the programmable control system and the remote controller processor are configured to actuate the haptic actuator when one of the catheter tip and the catheter positioning device reaches a position limit or an orientation limit.

14. The catheter positioning system of claim 13, wherein the programmable control system and the remote controller processor are configured to actuate the haptic actuator to provide a level of haptic feedback based on a user profile setting.

15. The catheter positioning system claim 11, wherein the first axis of the thumb joystick control and the second axis of the first wheel control are approximately parallel but offset from one another.

16. The catheter positioning system of claim 11, wherein:
the first wheel control and the second wheel control are configured to provide coarse adjustments of one or more of the rotational position, the linear position, and the bending position; and
the thumb joystick control is configured to provide a fine adjustment of one or more of the rotational position, the linear position, and the bending position.

17. The catheter positioning system of claim 11, wherein:
the thumb joystick control is configured as a four way switch; and
the first wheel control and the second wheel control provide adjustments of the one or more of the rotational position, the linear position, and the bending position.

18. The catheter positioning system of claim 17, wherein the thumb joystick control is configured as a momentary switch.

19. The catheter positioning system of claim 11, wherein the programmable control system further comprises a programmable control system processor and a storage device coupled to the programmable control system processor, wherein the programmable control system processor is configured with processor executable instructions to perform operations further comprising storing one or more user configurable settings associated with the remote controller.

20. The catheter positioning system of claim 19, wherein the one or more user configurable settings comprises one or more of: a sensitivity, a friction, a speed of rotation, a speed of extension, a speed of retraction, a brightness, a haptic feedback and a resolution of one or more of the thumb joystick control, the first wheel control, the second wheel control, the first indicator, the second indicator, and the third indicator.

21. The catheter positioning system of claim 11, wherein the remote controller processor is configured with processor executable instructions to perform operations further comprising maintaining a database of a plurality of user configurable settings associated with the remote controller for a plurality of users.

22. A catheter positioning system, comprising:
   a catheter positioning device;
   a programmable control system coupled to the catheter positioning device; and
   a remote controller comprising:
      a body that is semi-transparent;
      an illumination source within the body, wherein the illumination source is configured to illuminate the body;
      a thumb joystick control extending from a top side of the body;
      a first wheel control passing through the body and configured to rotate about a first axis of the remote controller, a first portion of the first wheel control extending from a first side of the body and a second portion of the first wheel control extending from a second side of the body opposite the first side;
      a second wheel control attached to a third side of the body and configured to rotate about a second axis of the remote controller, wherein the thumb joystick control, the first wheel control and the second wheel control are configured to control a position of a catheter tip;
      a first indicator configured to generate a first indication of one or more of a bending position and a linear position of the catheter tip;
      a second indicator configured to generate a second indication of a rotational position of the catheter tip;
      a third indicator configured to generate a third indication of a number of rotations of the catheter tip;
      a transceiver configured to transmit or receive signals between the remote controller and the programmable control system; and
      a remote controller processor coupled the illumination source, the thumb joystick control, the first wheel control, the second wheel control, the first indicator, the second indicator, the third indicator, and the transceiver, wherein the remote controller processor is configured to receive user input via at least one of the thumb joystick control, first wheel control, and second wheel control and, in response to the received user input, to send commands via the transceiver to the programmable control system for controlling operations of the catheter positioning device to control the position of the catheter tip, wherein the remote controller processor is configured with processor executable instructions to perform operations comprising controlling the illumination source based on a status of the catheter positioning device.

* * * * *